(12) United States Patent
Nwulia

(10) Patent No.: US 9,101,652 B2
(45) Date of Patent: Aug. 11, 2015

(54) METHOD, APPARATUS AND KIT FOR THE TREATMENT OF NEURODEGENERATIVE DISEASES AND IMPAIRMENTS

(71) Applicant: Howard University, Washington, DC (US)

(72) Inventor: Evaristus A. Nwulia, Ellicott City, MD (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 13/793,592

(22) Filed: Mar. 11, 2013

(65) Prior Publication Data

US 2014/0050806 A1  Feb. 20, 2014

Related U.S. Application Data

(60) Provisional application No. 61/684,316, filed on Aug. 17, 2012.

(51) Int. Cl.
| | |
|---|---|
| *A01N 65/00* | (2009.01) |
| *A61K 36/752* | (2006.01) |
| *A61K 36/54* | (2006.01) |
| *A61K 36/53* | (2006.01) |
| *A61K 9/00* | (2006.01) |
| *A61M 16/00* | (2006.01) |
| *A61M 16/12* | (2006.01) |
| *A61K 36/00* | (2006.01) |
| *A61M 16/06* | (2006.01) |
| *A61M 21/00* | (2006.01) |

(52) U.S. Cl.
CPC .............. *A61K 36/752* (2013.01); *A61K 9/007* (2013.01); *A61K 9/0043* (2013.01); *A61K 36/00* (2013.01); *A61K 36/53* (2013.01); *A61K 36/54* (2013.01); *A61M 16/0057* (2013.01); *A61M 16/12* (2013.01); *A61M 16/0666* (2013.01); *A61M 21/00* (2013.01); *A61M 2016/003* (2013.01); *A61M 2021/0016* (2013.01)

(58) Field of Classification Search
CPC ..... A61K 36/00; A61K 36/53; A61K 36/752; A61K 36/8962
USPC ........................................................ 424/725
See application file for complete search history.

(56) References Cited

U.S. PATENT DOCUMENTS

| | | | |
|---|---|---|---|
| 5,522,253 A | 6/1996 | Knight | |
| 5,875,783 A | 3/1999 | Kullik | |
| 6,145,503 A | 11/2000 | Smith | |
| 6,506,801 B1 | 1/2003 | Yee et al. | |
| 7,013,889 B2 | 3/2006 | Cronk et al. | |
| 7,273,618 B2 | 9/2007 | Frey, II et al. | |
| 7,703,455 B2 | 4/2010 | Bunke et al. | |
| 7,776,312 B2 | 8/2010 | Frey, II et al. | |
| 7,799,337 B2 | 9/2010 | Levin | |
| 8,001,968 B2 | 8/2011 | Doty et al. | |
| 8,192,718 B1 | 6/2012 | Sung et al. | |
| 8,220,457 B2 | 7/2012 | Berthon-Jones et al. | |
| 2004/0014721 A1 | 1/2004 | Hensley et al. | |
| 2005/0090520 A1 | 4/2005 | Lindquist | |
| 2011/0129462 A1 | 6/2011 | Maggio | |

OTHER PUBLICATIONS http://www.neurodegenerationresearch.eu/about/why/, 2014.*
Kat Snodgrass, Alzheimer's protein kills nerve cells in nose, [online]. Retrieved from the Internet on July 11, 2012. <URL: http://www.eurekalert.org/pub_releases/2011-09/sfn-apk092611.php>, Sep. 27, 2011, 1 page.
Robert S. Wilson et al., Odor Identification and Mortality in Old Age, Chemical Senses, Jan. 2011, 36(1), pp. 63-67.
Bamini Gopinath et al., The Association Between Olfactory Impairment and Total Mortality in Older Adults, The Journals of Gerontology, Series A, Biological Sciences and Medical Services, Feb. 2012, 67(2), pp. 204-209.
Yang Ruan et al., Olfactory Dysfunctions in Neurodegenerative Disorders, Journal of Neuroscience Research, Sep. 2012, 90(9), pp. 1693-1700.
Helen E. Scharfman and Moses V. Chao, The Entorhinal Cortex and Neurotrophin Signaling in Alzheimer's Disease and Other Disorders, Cognitive Neuroscience, Sep.-Dec. 2013, 4(3-4), pp. 123-135.
Richard L. Doty et al., Presence of Both Odor Identification and Detection Deficits in Alzheimer's Disease, Brain Research Bulletin, May 1987, 18(5), pp. 597-600.
Claire Murphy et al., Olfactory Thresholds are Associated with Degree of Dementia in Alzheimer's Disease, Neurobiology of Aging, Jul.-Aug. 1990, 11(4), pp. 465-469.
Raquelle I. Mesholam et al., Olfaction in Neurodegenerative Disease: A Meta-Analysis of Olfactory Functioning in Alzheimer's, and Parkinson's Diseases, Archives of Neurology, Jan. 1998, 55(1), pp. 84-90.
D. P. Devanand et al., Olfactory Deficits in Patients with Mild Cognitive Impairment Predict Alzheimer's Disease at Follow-up, The American Journal of Psychiatry, Sep. 2000, 157(9), pp. 1399-1405.
Mark W. Albers et al., At the Interface of Sensory and Motor Dysfunctions and Alzheimer's Disease, Alzheimer's & Dementia, Jan. 2015, 11(1), pp. 70-98.
Toshiko Atsumi and Keiichi Tonosaki, Smelling lavender and rosemary increases free radical scavenging activity and decreases cortisol level in saliva, Psychiatry Research, vol. 150, 2007, pp. 89-96.
Giacinto Bagetta et al., Neuropharmacology of the essential oil of bergamot, Fitoterapia, vol. 81, 2010, pp. 453-461.

(Continued)

*Primary Examiner* — Michael Meller
(74) *Attorney, Agent, or Firm* — Fitch, Even, Tabin & Flannery, LLP

(57) ABSTRACT

A method, apparatus and kit have been discovered which regenerate with the use of odorants the connections of the neurons of the brain and central nervous system in the treatment of such person afflicted neuro-disorders caused by disease or trauma.

6 Claims, 5 Drawing Sheets

(56) References Cited

OTHER PUBLICATIONS

Xue-Feng Bai et al., Nasal administration of myelin basic protein prevents relapsing experimental autoimmune encephalomyelitis in DA rats by activating regulatory cells expressing IL-4 and TGF-β mRNA, Journal of Neuroimmunology, vol. 80, 1997, pp. 65-75.
Christian Benedict et al., Intranasal insulin improves memory in humans, Psychoneuroendocrinology, vol. 29, 2004, pp. 1326-1334.
Jan Born et al., Sniffing neuropeptides: a transnasal approach to the human brain, Nature Neuroscience, vol. 5, No. 6, Jun. 2002, pp. 514-516.
Serena Bovetti et al., Olfactory Enrichment Influences Adult Neurogenesis Modulating GAD67 and Plasticity-Related Molecules Expression in Newborn Cells of the Olfactory Bulb, PLoS ONE, vol. 4, Issue 7, Jul. 2009, 10 pages.
Ilaria Ceccarelli et al., Effects of long-term exposure of lemon essential oil odor on behavioral, hormonal and neuronal parameters in male and female rats, Brain Research, vol. 1001, 2004, pp. 78-86.
Xue-Qing Chen et al., Delivery of Nerve Growth Factor to the Brain via the Olfactory Pathway, Journal of Alzheimer's Disease, vol. 1, 1998, pp. 35-44.
Eain M. Comford and Marcia E. Comford, New systems for delivery of drugs to the brain in neurological disease, The Lancet Neurology, vol. 1, Sep. 2002, pp. 306-315.
Richard M. Costanzo, Neural Regeneration and Functional Reconnection Following Olfactory Nerve Transection in Hamster, Brain Research, vol. 361, 1985, pp. 258-266.
Nicole Etchamendy et al., Alleviation of a Selective Age-Related Relational Memory Deficit in Mice by Pharmacologically Induced Normalization of Brain Retinoid Signaling, The Journal of Neuroscience, Aug. 15, 2001, vol. 21, No. 16, pp. 6423-6429.
Claudia Brito Faturi et al., Anxiolytic-like effect of sweet orange aroma in Wistar rats, Progress in Neuro-Psychopharmacology & Biological Psychiatry, vol. 34, 2010, pp. 605-609.
Gilles Gheusi et al., Importance of newly generated neurons in the adult olfactory bulb for odor discrimination, Proceedings of the National Academy of Sciences, vol. 97, No. 4, Feb. 15, 2000, pp. 1823-1828.
Illana Gozes, Neuroprotective peptide drug delivery and development: potential new therapeutics, Trends in Neurosciences, vol. 24, No. 12, Dec. 2001, pp. 700-705.
Pasquale P. C. Graziadei et al., Regeneration of olfactory axons and synapse formation in the forebrain after bulbectomy in neonatal mice, Proceedings of the National Academy of Sciences of the United States of America, vol. 75, No. 10, Oct. 1978, pp. 5230-5234.
P. P. C. Graziadei and G. A. Monti Graziadei, Neurogenesis in neuron regeneration in the olfactory system of mammals. I. Morphological aspects of differentiation and structural organization of the olfactory sensory neurons, Journal of Neurocytology, vol. 8, 1979, pp. 1-18.
Joseph W. Harding et al., Denervation of the Primary Olfactory Pathway in Mice. V. Long-term Effect of Intranasal ZnSO4 Irrigation on Behavior, Biochemistry and Morphology, Brain Research, vol. 140, 1978, pp. 271-285.

Migiwa Komiya et al., Lemon oil vapor causes an anti-stress effect via modulating the 5-HT and DA activities in mice, Behavioural Brain Research, vol. 172, 2006, pp. 240-249.
Kai Liao et al., Enriched odor exposure decrease tau phosphorylation in the rat hippocampus and cortex, Neuroscience Letters, vol. 507, 2012, pp. 22-26.
Nathalie Mandairon et al., Broad activation of the olfactory bulb produces long-lasting changes in odor perception, Proceedings of the National Academy of Sciences of the United States of America, vol. 103, No. 36, Sep. 5, 2006, pp. 13543-13548.
Marcela Martončíková et al., Odor enrichment influences neurogenesis in the rostral migratory stream of young rats, Acta Histochemica, vol. 113, 2011, pp. 326-332.
Patrick Maxwell and Konstantin Salnikow, HIF-1 An Oxygen and Metal Responsive Transcription Factor, Cancer Biology & Therapy, vol. 3, No. 1, Jan. 2004, pp. 29-35.
Naofumi Miwa and Daniel R. Storm, Odorant-Induced Activation of Extracellular Signal-Regulated Kinase/Mitogen-Activated Protein Kinase in the Olfactory Bulb Promotes Survival of Newly Formed Granule Cells, The Journal of Neuroscience, vol. 25, No. 22, Jun. 1, 2005, pp. 5404-5412.
Christelle Rochefort et al., Enriched Odor Exposure Increases the Number of Newborn Neurons in the Adult Olfactory Bulb and Improves Odor Memory, The Journal of Neuroscience, vol. 22, No. 7, Apr. 1, 2002, pp. 2679-2689.
T. M. Ross et al., Intranasal administration of interferon beta bypasses the blood-brain barrier to target the central nervous system and cervical lymph nodes: a non-invasive treatment strategy for multiple sclerosis, Journal of Neuroimmunology, vol. 151, 2004, pp. 66-77.
Somrudee Saiyudthong and Charles A. Marsden, Acute Effects of Bergamot Oil on Anxiety-Related Behavious and Corticosterone Level in Rats, Phytotherapy Research, vol. 25, 2011, pp. 858-862.
Carla Schulz et al., Central Nervous and Metabolic Effects of Intranasally Applied Leptin, Endocrinology, vol. 145, No. 6, Jun. 2004, pp. 2696-2701.
Lee A. Shapiro et al., Olfactory enrichment enhances the survival of newly born cortical neurons in adult mice, NeuroReport, vol. 18, No. 10, Jul. 2, 2007, pp. 981-985.
Peter A. Simmons and Thomas V. Getchell, Physiological Activity of Newly Differentiated Olfactory Receptor Neurons Correlated With Morphological Recovery From Olfactory Nerve Section in the Salamander, Journal of Neurophysiology, vol. 45, No. 3, Mar. 1981, pp. 529-549.
Eugene D. Weinberg and Judity Miklossy, Iron Withholding: A Defense Against Disease, Journal of Alzheimer's Disease, vol. 13, 2008, pp. 451-463.
Cynthia C. Woo et al., Exposure to a broad range of odorants decreases cell mortality in the olfactory bulb, NeuroReport, vol. 17, No. 8, May 29, 2006, pp. 817-821.
Steven L. Youngentob et al., Odorant Threshold Following Methyl Bromide-Induced Lesions of the Olfactory Epithelium, Physiology & Behavior, vol. 62, No. 6, 1997, pp. 1241-1252.

* cited by examiner

METHOD, APPARATUS AND KIT FOR THE TREATMENT OF NEURODEGENERATIVE DISEASES AND IMPAIRMENTS

This application claims the benefit of U.S. Provisional Application Ser. No. 61/684,316, filed Aug. 17, 2012 which is incorporated herein as if fully rewritten.

FIELD

Described herein is a method, apparatus and kit for the treatment of neurodegenerative diseases and impairments with the use of odorants.

BACKGROUND

Alzheimer's disease and dementia are diseases which result in a progressive deterioration of neurons in the brain which causes cognitive deterioration and changes in behavior. With Alzheimer's disease, there is loss of short-term memory and minor forgetfulness which becomes greater as the illness progresses to major memory loss with a relative preservation of older memories. As the disease progresses even further, there is cognitive or intellectual impairment which extends to language degeneration (having difficulty remembering words to being completely unable to speak, read, or write), loss of the ability to execute or carry out learned purposeful movements, and a loss of ability to recognize objects, persons, sounds, shapes, or smells.

Neurons are cells which transmit information via synapses. Neurons connect to each other to form neural networks. Neurons are electrically excitable cells which transmit information by electrical and chemical signaling by synapses which establish connections with other neuron cells. With the progression of Alzheimer's disease and other neurodegenerative diseases, the connectivity of the neurons are adversely affected, such as by the generation of plaque and abnormal proteins called tau proteins.

SUMMARY

The olfactory system beginning in the nose and ending in the cortex and central structures of the brain is the only part of the adult mammalian brain capable of stimulation and regeneration. A method, apparatus and kit have been discovered which regenerate the connections of the neurons of the brain and central nervous systems such that connectivity of the neurons is improved to effect improvement in memory loss, language degeneration, loss of the ability to execute or carry out learned purposeful movements, and a loss of ability to recognize objects, persons, sounds, shapes, or smells. The method includes the delivery of a blend of olfactory enrichment odorants to and through the nose with the delivery of the odorants being under a positive pressure to affect air flow with the odorant at a room temperature (25 degrees C.) delivery rate of air containing odorant of from about 0.5 to about 2 liters per minute. Stimulation of the olfactory neurons in the nose by the odorant blend stimulate neurogeneis (new brain development) in the olfactory brain regions affected neuro-impairments caused by disease or trauma including a cognitive impairment which is a prodromal state in the development of dementia, traumatic brain injury affecting the olfactory regions of the brain, including the frontal lobe, post stroke brain damage involving the frontal lobe regions and olfactory cortices of the brain, Parkinson's disease, schizophrenia and chronic depression. The stimulation of neurogeneis effects a reversal of brain impairments caused by the latter diseases and injuries. In a very important aspect, stimulation of the olfactory neurons in the nose by the odorant blend stimulate neurogeneis in the olfactory brain regions affected by Alzheimer's and other types of dementia and reverse neuropathologies of Alzheimer's disease and dementia, namely hyperphoshorylation of neurofibrillary tangles and tau proteins. The blend of odorants includes a blend of a plurality of odors including citrus (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise at a positive pressure to affect air flow with the odorant delivery rate of from about 0.5 to about 2 liters per minute. In an important aspect, at least three of the odors should be used. And in a very important aspect, the odorants include a blend of citrus (orange), lemon, rosemary and cinnamon at a positive pressure to affect air flow with the odorant delivery rate of from about 0.5 to about 2 liters per minute. The odorants are dispersed in a media which permits them to be swept into the nose for intranasal application of the odorants. In an important aspect, the media is a pharmaceutically acceptable oil, such as mineral oil.

The odorants are in a concentration for each odorant in the range of from about 1 to about 6 weight percent and are driven through the nose to contact olfactory tissue and olfactory receptor neurons. The method brings odorants in contact to this tissue in constant flow or pressure, which is needed to stimulate regeneration (or birth) of olfactory sensory system, which in turn, stimulates the olfactory bulb and olfactory cortices to be active by the intranasal administration of a blend of odorants dispersed in a media, the odorant blend including at least two, preferably three, of the odorants citrus (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise by pumping the blend as part of a flow of gas which includes oxygen and odorant blend. The flow created by a pump creates a positive pressure to create a flow of oxygen and odorant blend through the nose. The concentration of the blend, the ratio of odorants, the rate of flow of the blend and oxygen, a time of treatment, and the ratios of odorants in the blend effective for effecting an improved neuro-function of a person afflicted with the neurodegenerative disease or trauma. In an important aspect for a subject afflicted with a neurrodgenerative disease such as Alzheimer's disease and/or dementia, the concentration of the odorant blend, the ratio of odorants, the rate of flow of the blend and oxygen, a time of treatment, and the ratios of odorants in the blend effective for effecting an improvement of at least 50%, preferably 100% and even more preferably 150% in short-term verbal memory of a person afflicted with the neurodegenerative disease, the improvement being measured by a California Verbal Learning Test, Adult, Version 2. The time of treatment is from about 12 hours daily for at least about two weeks, and preferably, for at least about one month. The method contemplates a treatment with a concentration of odorants at positive pressures for a time which effects new brain development (i.e. neuroplasticity) and reversal of pathological features of Alzheimer's disease or dementia in mammals.

The apparatus used to deliver the odorants includes a pump, an air filter, a flow meter, a check valve, an odorant chamber and a cannula configured to deliver the odorant to users afflicted with the neuro degeneration disease. The odorant chamber contains the blend of odorants which are pleasant, tolerable and effect enrichment to human memory after or during the deleterious effects of Alzheimer's disease and dementia and other neurodegenerative diseases. The pump generates a current of filtered air directed into the odorant chamber through a tube with flow-directed valves. This flow is channeled through a user-controlled flow meter, on the outside of the device, for regulation of the rate of flow of odorant containing air/oxygen to the nose. The cannula directing the flow to the nose comes in different shapes and sizes, depending on the shape of a user's nose. The inside of human nose is enriched as the odorants exit the cannula and contact olfactory tissue.

In another aspect, a kit is provided where the kit which includes an apparatus which is configured for the administration of a blend of odorants. The apparatus in the kit comprises a pump; a line which is effective for supplying air to a vessel configured to contain a blend of odorants; a line from the vessel to a cannula configured for lodgment into the nose, the pump being configured to provide a positive pressure and a flow of gas into the cannula and nose at a rate of from about 0.5 to about 2 liters per minute; and at least one additional vessel which includes a second vessel containing a blend of odorants; and wherein the odorant blend in the second vessel includes citrus, lemon, rosemary and cinnamon. The kit is configured for administering the blend including pumping the blend as a part of a flow of gas which includes oxygen and odorant blend. The flow created by the pump creates a positive pressure to create a flow of oxygen and odorant blend through the nose. The concentration of the blend, the ratio of odorants, the rate of flow of the blend and oxygen, a time of treatment, and the ratios of odorants in the blend are effective for effecting an improvement of at least 50%, preferably 100% and even more preferably 150% in short-term verbal memory of a person afflicted with the neurodegenerative disease, the improvement being measured by a California Verbal Learning Test, Adult, Version 2. The kit also may include instructions as to the time of administration of the blend, such as 12 hours daily for one month.

FIGURES

DETAILED DESCRIPTION

Figure 1:
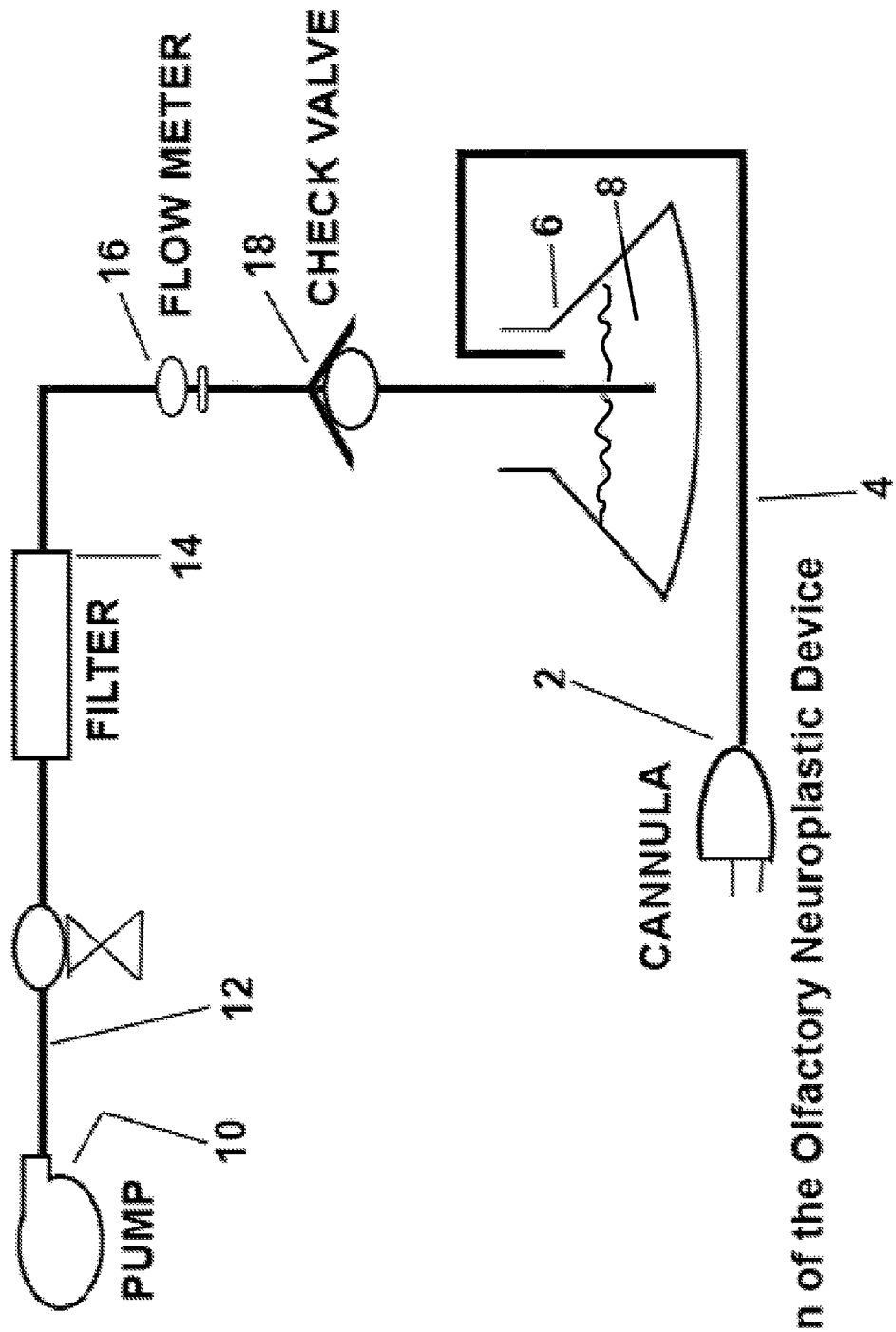
FIG. 1 is an illustration of the device used to practice the method described herein.
Figure 2:
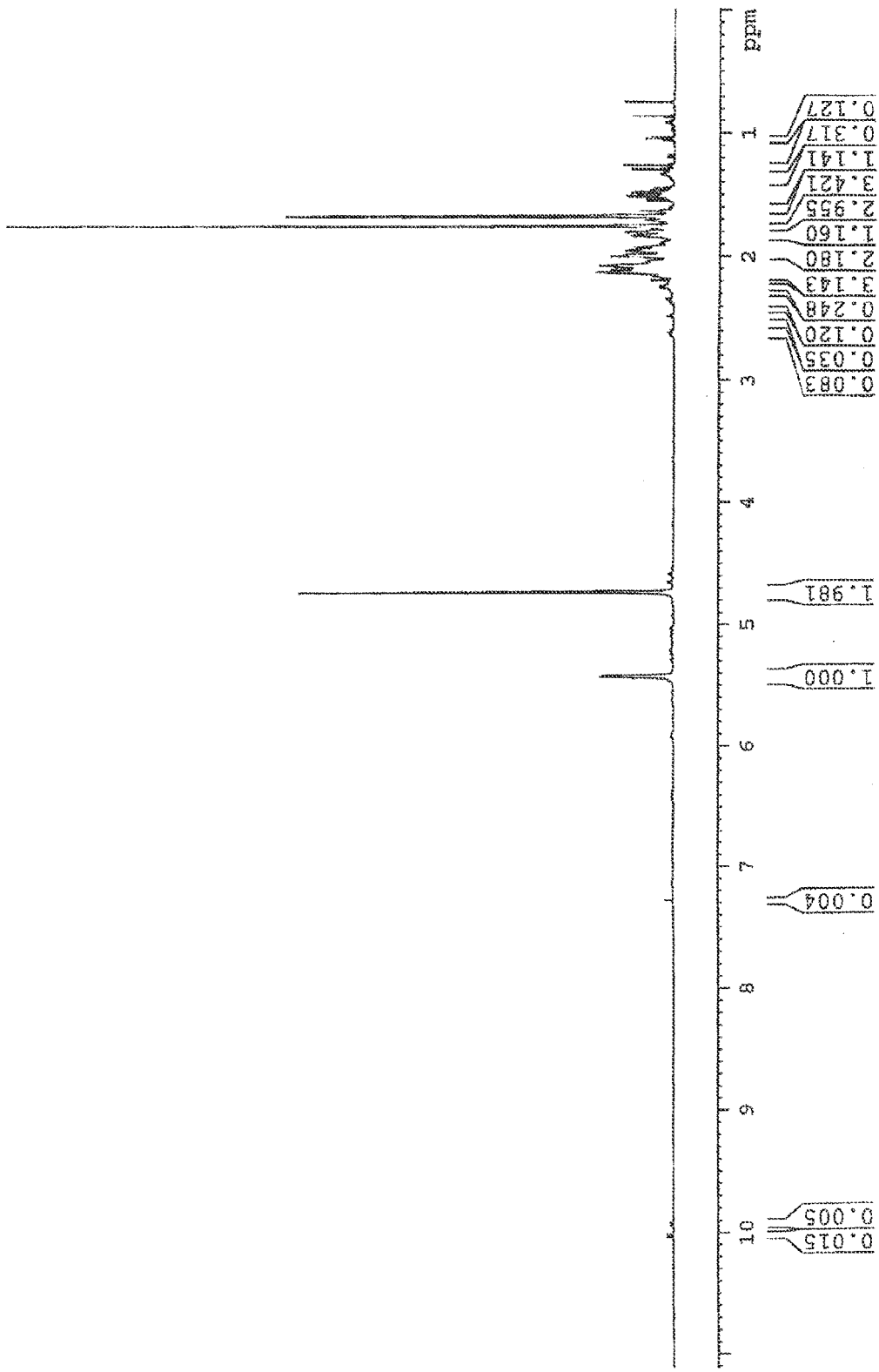
FIG. 2 illustrates a Nuclear Magnetic Resonance spectra of the odorant of lemon.
Figure 3:
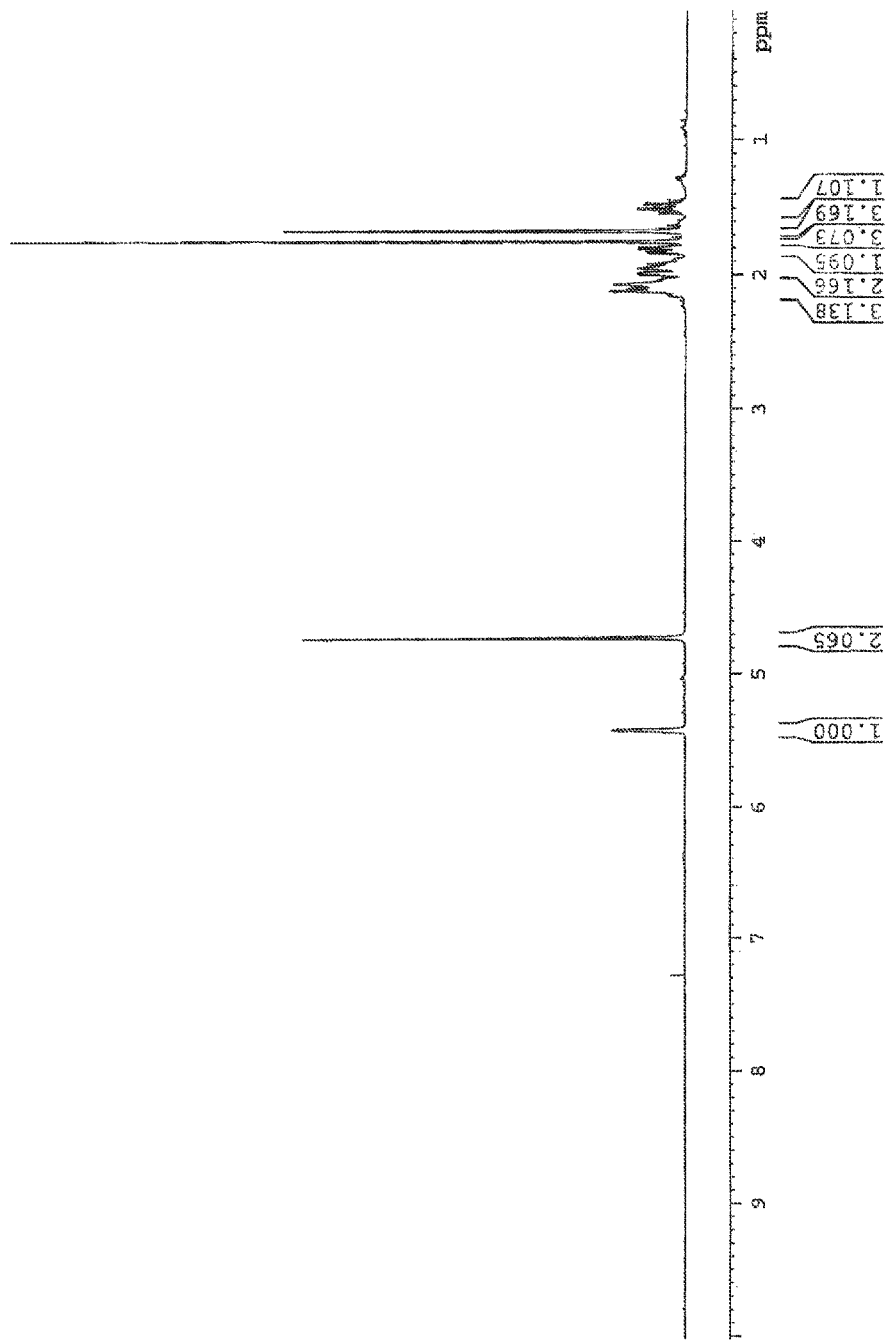
FIG. 3 illustrates a Nuclear Magnetic Resonance spectra of the odorant of sweet orange.
Figure 4:
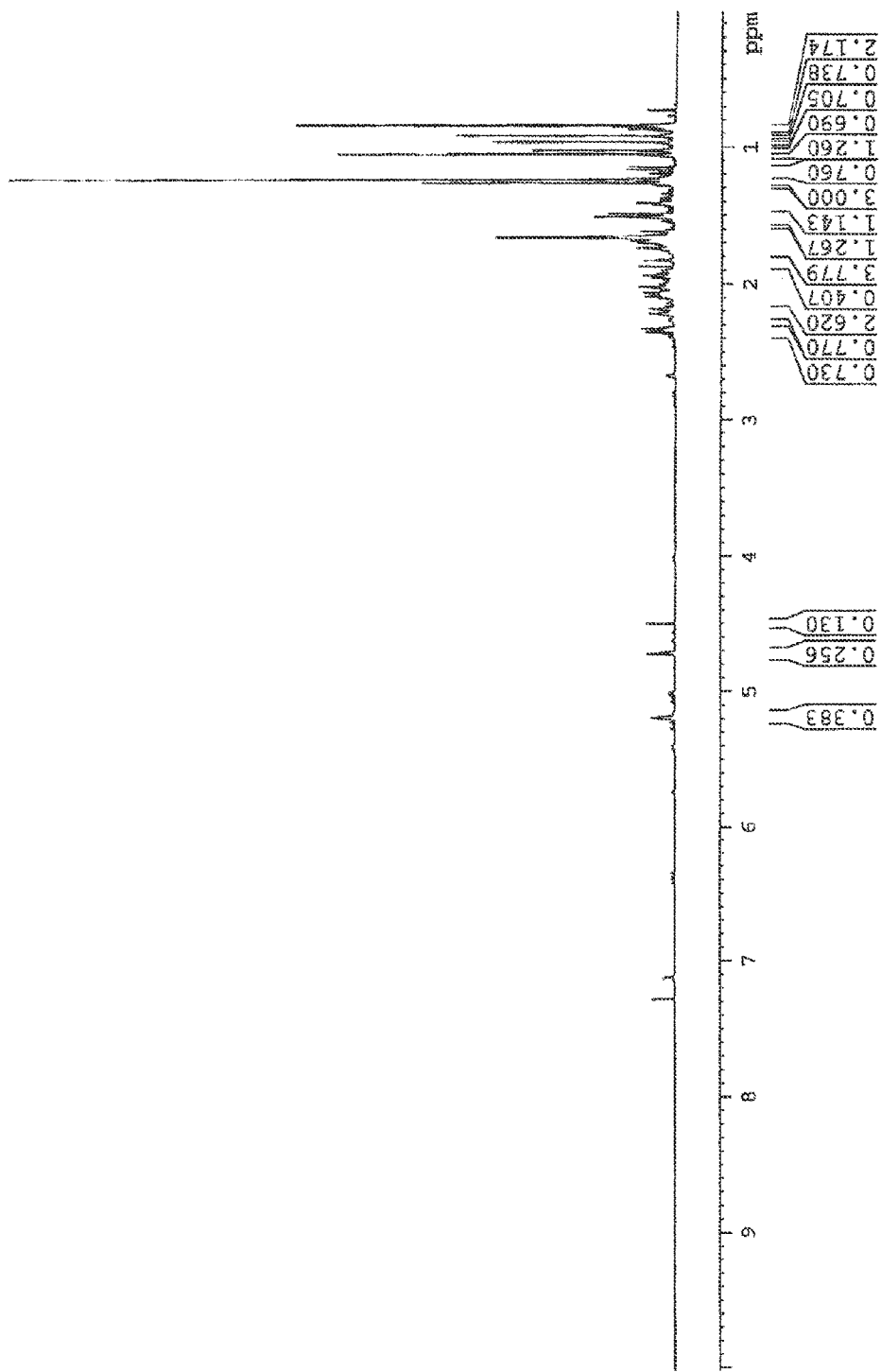
FIG. 4 illustrates a Nuclear Magnetic Resonance spectra of the odorant of rosemary.
Figure 5:
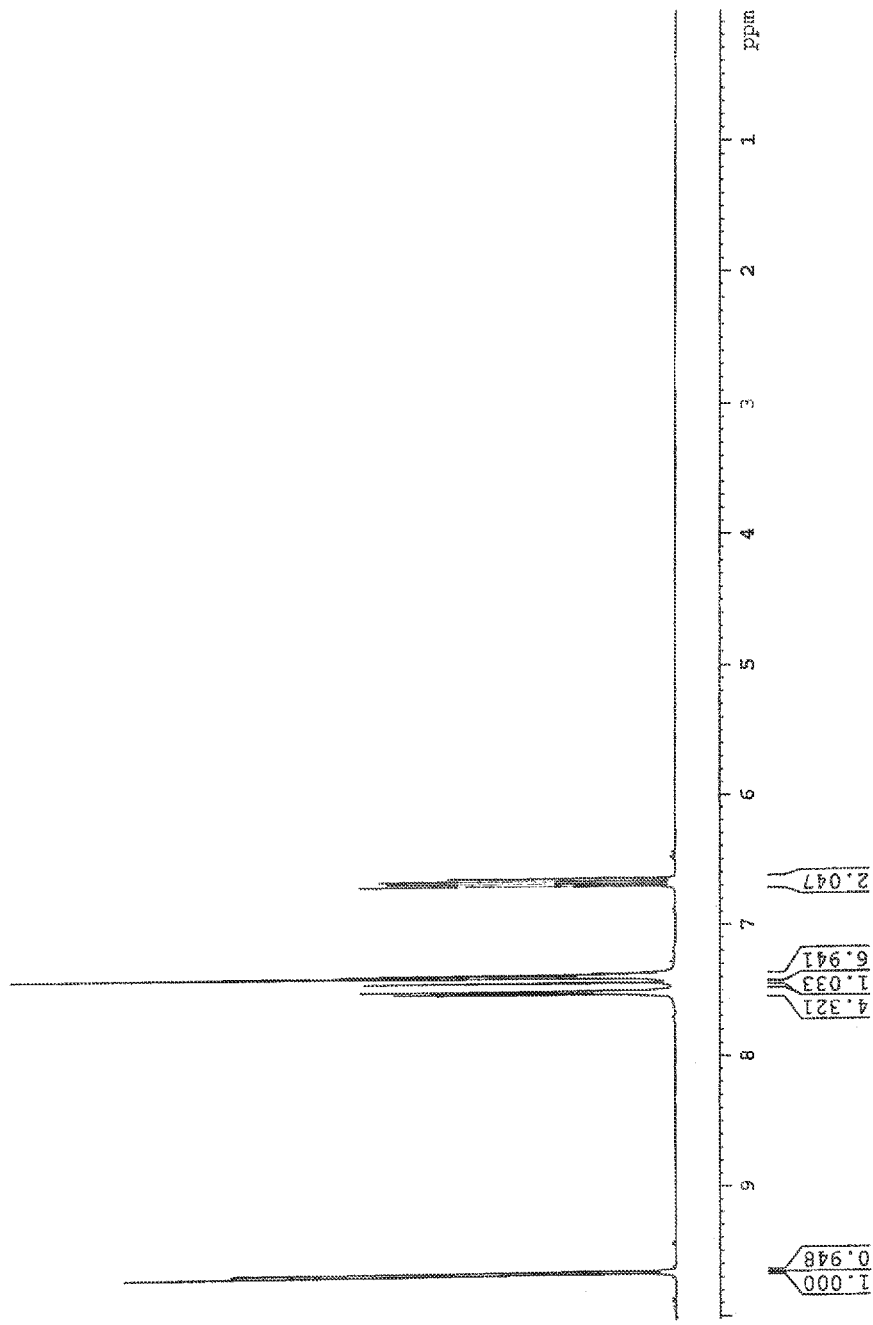
FIG. 5 illustrates a Nuclear Magnetic Resonance spectra of the odorant of cinnamon.

The apparatus includes cannula 2 having a conduit 4 into an odorant chamber 6 containing a blend of odorants 8. Pump 10 pumps air at a positive pressure through conduit 12 to filter 14 and flow meter 16 past check valve 18 into the odorant chamber 6. The air under positive pressure sweeps the odorants from the blend of odorants into conduit 4 and pushes the odorants through cannula 2 into the nose of the user.

In the important aspect, the blend of odorants includes sweet orange also called citrus sinensis. Bergamont orange also called citrus bergamia also can be used in lieu of sweet orange or blended with sweet orange. The blend further includes lemon oil also called citrus limon. As used herein, "citrus," as opposed to "citrus limon" means sweet orange or bergamont orange. The odorant blend also includes Cinnamon oil also known as cinnamomum zeylanicum and rosemary oil also called rosmarinus officinalis. Odorants which are not from a botanical source such as cinnamonum zeylanicum, but are flavorings which mimic the botanical sourced odorant also may be used. The individual odorants range in concentration of from about 0.5 weight percent to about 6.0 weight percent in the odorant chamber 6 and are delivered at an air/odorant rate of from about 0.5 to about 2 liters per minute. The odorant are diluted in mineral oil to obtain the latter concentration range. The device is powered by electricity through a 9V adapter plugged to any electrical source, such as a wall outlet.

In an important aspect, the apparatus is portable to permit treatment over a day/evening. In this aspect, the pump is operated with DC current being supplied by a rechargeable battery. The apparatus has a housing to accommodate the battery and an outlet to effect recharging.

Tests involving a blend of sweet orange, bergamont orange, citrus limon, cinnamon and rosemary were conducted on volunteers with each odorant dispersed in mineral oil at a concentration of 3 weight percent at an air/odorant flow rate of 0.5 liters/minute. The subjects were subjected to application of the odorant blend at the aforedescribed positive pressure for two weeks at 12 hours per day. Tests of memory functions are shown in the table below:

| CVLT Recognition/Recall | Pre-OND | Post-OND |
|---|---|---|
| Total Recognition Raw Score | 12 | 16 |
| Recognition Z score | −2.5 | 0 |
| Total False Positives | 10 | 0 |
| Total False Positives Z | 3.5 | −0.5 |
| Short Delay Free Recall | 5 | 15 |
| Short Delay Free Recall Z | −3 | 1 |
| Short Delay Cued Recall | 6 | 16 |
| Short Delay Cued Recall Z | −3 | 1 |

The result support increased recognition and markedly increased free by 200% and cued by 150% short-term memory recall in this volunteer following Olfactory Treatment Delivery System (OND treatment). Moreover, it was found that the treatment increased the sense of smell. Of two volunteers, one had a remarkable anosmia and was unable to identify the n-butanol odorant at the maximum concentration supplied in the olfact-combo olfactometer. After 4 weeks of OND, he identified up to the 6th dilution of the n-butanol (maximum is 9th dilution). Significant changes in the scores for odor identification, odor memory and odor discrimination were also observed for both volunteers.

What is claimed is:

1. A method for treating a human suffering from symptoms of dementia, the method comprising:
   intranasally administering to said human suffering from symptoms of dementia a blend of odorants dispersed in a pharmaceutically acceptable oil, wherein said blend of odorants are two or more odorants selected from the group consisting of citrus extract, rosemary extract, cinnamon extract, banana oil, cumin extract, vanillin extract, ethylvanillin extract, garlic extract, paprika extract, curry extract, nutmeg extract, thyme extract, tarragon extract, celery extract, ginger extract, lavender extract, marjoram extract, basil leaf extract, cardamom extract, clove extract, chocolate extract and anise extract, each of the blend of odorants dispersed in a pharmaceutically acceptable oil being present at an amount of about 0.5 wt. % to about 6 wt. %, the administering including pumping the blend of odorants as a part of a flow of gas which includes oxygen and the odorant blend, the flow created by a pump which creates a positive pressure to create a flow of oxygen and the odorant blend through the nose of the human at a rate of about 0.5 to about 2 liters per minute at 25° C., the concentration of the blend of odorants and the time of treatment of the human being therapeutically effective for an improvement of a neurofunction of the human afflicted with the symptoms of dementia by at least 50% in short-term verbal memory of the human suffering from symptoms of dementia, the improvement being measured by a California Verbal Learning Test, Adult, Version 2.

2. The method of claim 1 wherein the blend of odorants includes at least three of the odorants.

3. The method of claim 1 wherein the blend of odorants includes orange, lemon, rosemary and cinnamon.

4. The method of claim 1 wherein the administration of the blend of odorants is for at least about two weeks for periods of from about 12 hours per day.

5. The method of claim 1 wherein the administration of the blend of odorants is for at least one month.

6. The method of claim 1 wherein the pharmaceutically acceptable oil is mineral oil.

* * * * *